United States Patent [19]
Stratz, Sr.

[11] Patent Number: 5,615,682
[45] Date of Patent: Apr. 1, 1997

[54] ULTRASOUND TRANSDUCER CABLE MANAGEMENT SYSTEM

[75] Inventor: James R. Stratz, Sr., Barrington, N.H.

[73] Assignee: Hewlett-Packard Company, Palo Alto, Calif.

[21] Appl. No.: 548,510

[22] Filed: Oct. 26, 1995

[51] Int. Cl.[6] .................................................. A61B 8/00
[52] U.S. Cl. ................................................. 128/662.03
[58] Field of Search ..................... 128/660.01, 662.03; 29/745, 746, 747, 753, 754

[56] References Cited

U.S. PATENT DOCUMENTS

| 4,901,434 | 2/1990 | Sato et al. ................................. 29/753 |
| 5,129,397 | 7/1992 | Jingu et al. ........................... 128/660.01 |
| 5,402,971 | 4/1995 | Bower . | |
| 5,505,203 | 4/1996 | Deitrich et al. ...................... 128/660.01 |

Primary Examiner—George Manuel
Attorney, Agent, or Firm—John L. Imperato

[57] ABSTRACT

A cable management system organizes transducer cables connecting multiple transducer probes to a mobile ultrasound imaging system. The transducer cables and the cable management system form a cable array. Each transducer cable within the cable array is held by a retaining clip and rides in a common slot assembly. The retaining clips are suspended in the slot assembly by retaining rings. The cable management system slidably mounts multiple transducer cables on the mobile ultrasound imaging system, avoiding entanglement with casters of the mobile ultrasound imaging system and with other transducer cables in the cable array.

9 Claims, 3 Drawing Sheets 5,615,682

ULTRASOUND TRANSDUCER CABLE MANAGEMENT SYSTEM

FIELD OF THE INVENTION

This invention relates to a cable array for connecting multiple transducer probes to a medical ultrasound imaging system.

BACKGROUND OF THE INVENTION

Physicians and medical technicians use ultrasound imaging systems in a variety of medical imaging applications. In an attempt to fully utilize these expensive imaging systems, several specialized transducer probes, each designed to view a different part of the human body, are connected to a single imaging system. For example, a transthoracic probe for cardiac imaging, a Doppler probe for arterial blood flow imaging and an abdominal probe for soft tissue imaging of the stomach may each be connected to the imaging system using separate transducer cables. Typically, the imaging system has wheels to provide mobility, enabling the imaging system to be shared by physicians and technicians throughout a hospital or clinic. Because transducer cables are designed to be long enough to reach from the imaging system to a patient, when the imaging system is moved, the transducer cables often become entangled with the wheels, knocking the transducer probes to the ground. Transducer cables also become inter-twined with one another, causing transducer probes to fall to the ground, or otherwise, restricting maneuverability of a transducer probe while it is being used. Unfortunately, the transducer probes are easily damaged when dropped and they are expensive to repair or replace.

SUMMARY OF THE INVENTION

In accordance with the illustrated preferred embodiment of the present invention a cable management system collates transducer cables connecting multiple transducer probes to an ultrasound imaging system and reduces the risk of damage to transducer probes. The transducer cables and the cable management system form a cable array. Each transducer cable within the cable array is held by a retaining clip that is slidably mounted in a common slot assembly. The cable management system enables individual transducer probes to be used without entanglement by other transducer cables in the cable array, which reduces the likelihood of the transducer probes being knocked to the ground and reduces the risk of damage to the transducer probes.

DETAILED DESCRIPTION OF THE PREFERRED EMBODIMENT

Figure 1:
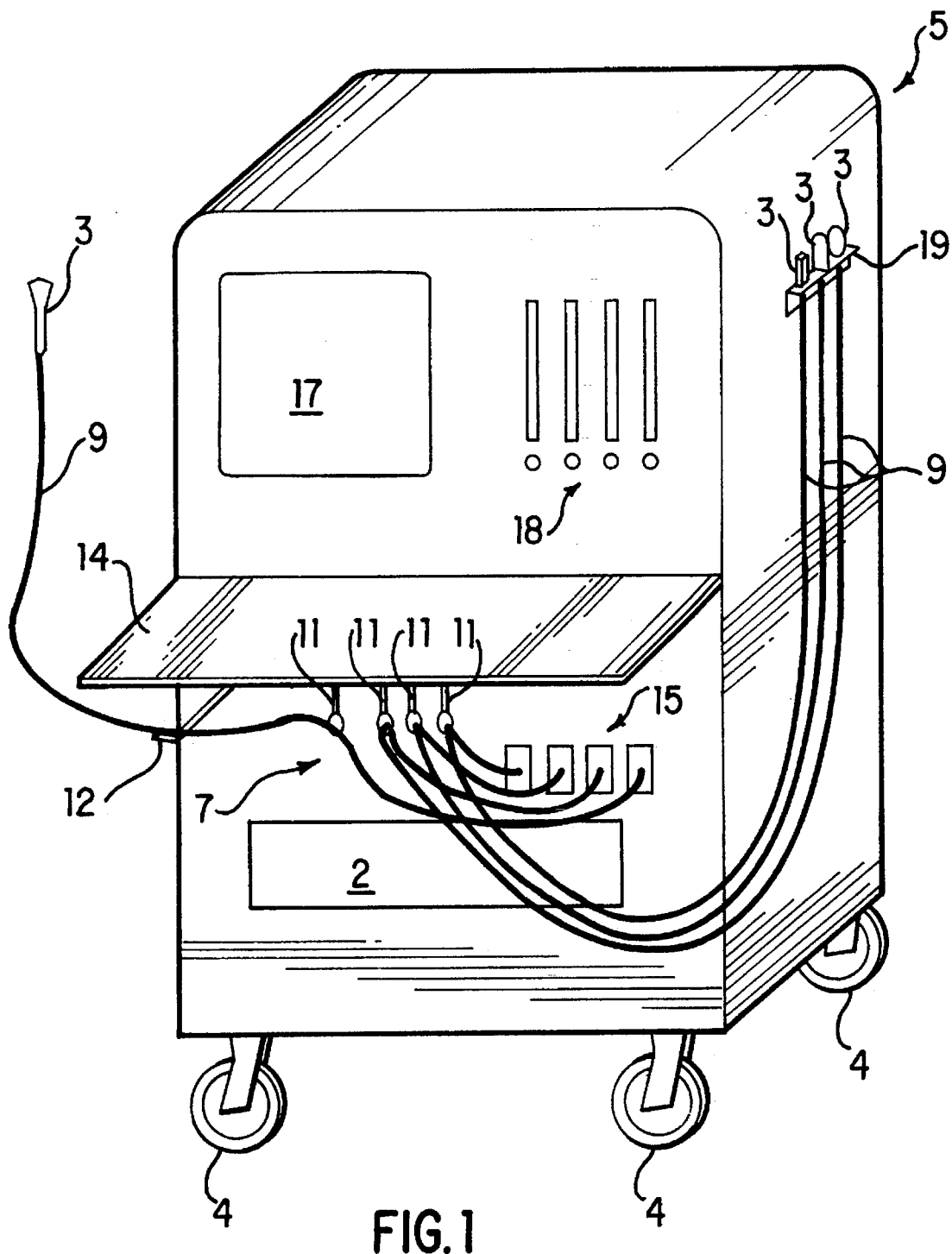
FIG. 1 shows an ultrasound imaging system including a cable array that is constructed in accordance to the illustrated preferred embodiment of the present invention.

FIG. 1 shows an ultrasound imaging system 5 including a cable array 7 that is constructed in accordance to the first illustrated preferred embodiment of the present invention. The cable array 7 includes transducer cables 9 and a cable management system. Retaining clips 11 and a mounting rod 12 which are parts of the cable management system, are shown. The cable management system prevents the transducer cables 9 from becoming entangled with each other and entangled with wheels or castors 4, used to transport the ultrasound imaging system 5. The retaining clips 11 with their corresponding transducer cables 9 slide from side to side, as necessary, to better maneuver transducer probes 3 attached to the transducer cables 9. While a peripheral component 2 such as a disk drive, tape deck or video printer is used to record ultrasound images by the physician or technician operating the ultrasound imaging system 5, the sliding action of the retaining clips 11 also provides access to the peripheral component 2.

Transducer cables 9 provide electrical connections between the transducer probes 3 and the ultrasound imaging system 5. A terminal 15 at the end of each transducer cable 9 joins the transducer cable to the ultrasound imaging system 5. To use the ultrasound imaging system 5, a transducer probe 3 is held by a physician or technician and is placed against a patient's skin. The transducer probe 3 uses ultrasound signals to ultrasonically interrogate the patient's body by transmitting an ultrasound signal and receiving the ultrasound signal after it is reflected by the patient's body. An ultrasound image of a patient's organs and tissues is viewed on a display 17 while adjustments to the ultrasound image are made using switches and knobs on a control panel 18. While transducer probes 3 are not used, they are held in place by a cable rack 19. A service tray 14 provides storage space for gels that are applied to the patient's skin, swabs used to wipe the gel from the patient, or other items.

Figure 2:
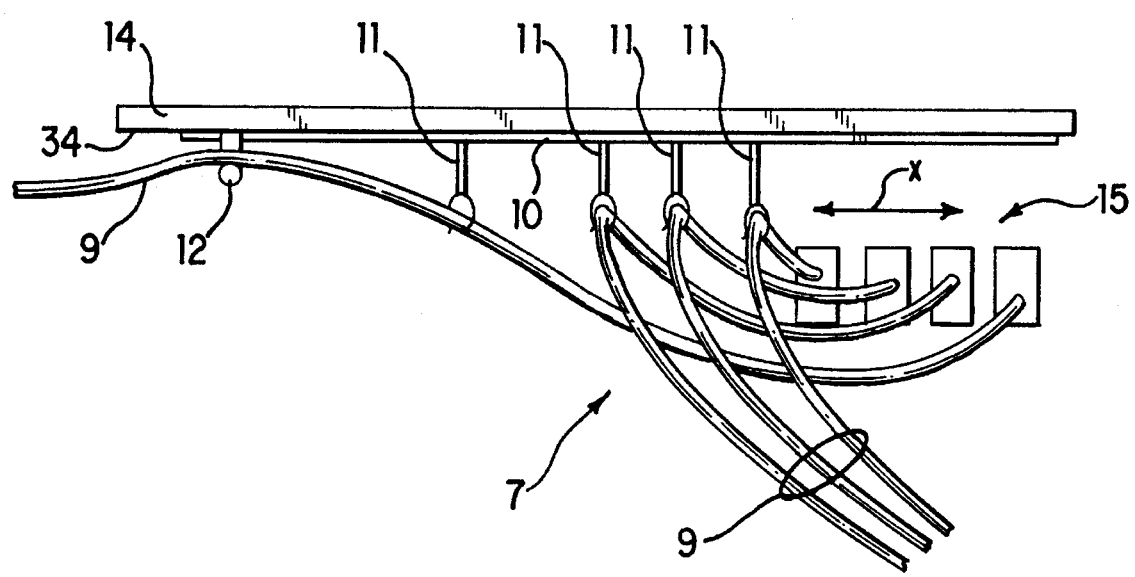
FIG. 2 shows a detailed view of the cable array of FIG. 1 including a cable management system that is constructed in accordance to the illustrated preferred embodiment of the present invention.

FIG. 2 shows a detailed view of the cable array 7 including a cable management system that is constructed in accordance to the illustrated preferred embodiment of the present invention. The cable array 7 includes a series of individual transducer cables 9 and a cable management system. The cable management system comprises a slot assembly 10, retaining clips 11 and an optional mounting rod 12. The retaining clips are held in place in the slot assembly 10 using retaining rings, not shown. The slot assembly 10 is shown mounted on the underside 34 of a service tray 14 attached to the ultrasound imaging system 5. In ultrasound imaging systems that do not have a service tray 14, the slot assembly 10 may be mounted on a surface of the ultrasound imaging system 5, such as the side or front. If the ultrasound system 5 lacks castors 4 and is instead mounted on a cart (not shown), the cart may then be considered to be part of the ultrasound system. The slot assembly 10 may also be attached to a part of the cart.

The retaining clips 11 secure the transducer cables 9 in a removable fashion to the slot assembly 10. If a transducer probe 3 replacement or transducer cable 9 replacement is needed, the transducer cable 9 is unfastened from the retaining clip 11. The retaining clips 11 hold the transducer cables 9 by pinching or encircling the transducer cable or by other suitable means. The retaining clips 11 are designed to slide within the slot assembly 10 in the lateral direction, indicated by arrows X, to provide maneuverability to transducer probes 3 attached to the transducer cables 9. The sliding action also provides access to peripheral components 2 behind the cable array 7. Depending on the surrounding environment in which the ultrasound imaging system is used, the transducer cable 9 may be re-positioned within the retaining clip 11 so as to secure the transducer cable 9 at a different point. The number of retaining clips 11 within the cable management system may be increased or decreased to correspond to the number of transducer cables 9, or a number of retaining clips 11 sufficient to accommodate the anticipated number of transducer cables 9 may be selected in advance.

A mounting rod 12 which is an optional element of the cable management system is shown secured to the bottom surface 34 of the service tray 14. In an alternative embodiment, the mounting rod 12 is attached to a surface of the imaging system 5. The mounting rod 12 is secured by screws, glue or other suitable attachment methods. The mounting rod 12 provides further convenience to the physician or technician operating the ultrasound imaging system by allowing a transducer cable 9 to be draped over the mounting rod 12. The mounting rod 12 enables a particular transducer cable 9 of the cable array 7 to remain separated from other transducer cables 9. The mounting rod 12 is either hook shaped or "J" shaped, or even a straight rod positioned in an upward direction, as to accommodate a transducer cable 9 draped over it.

Figure 3:
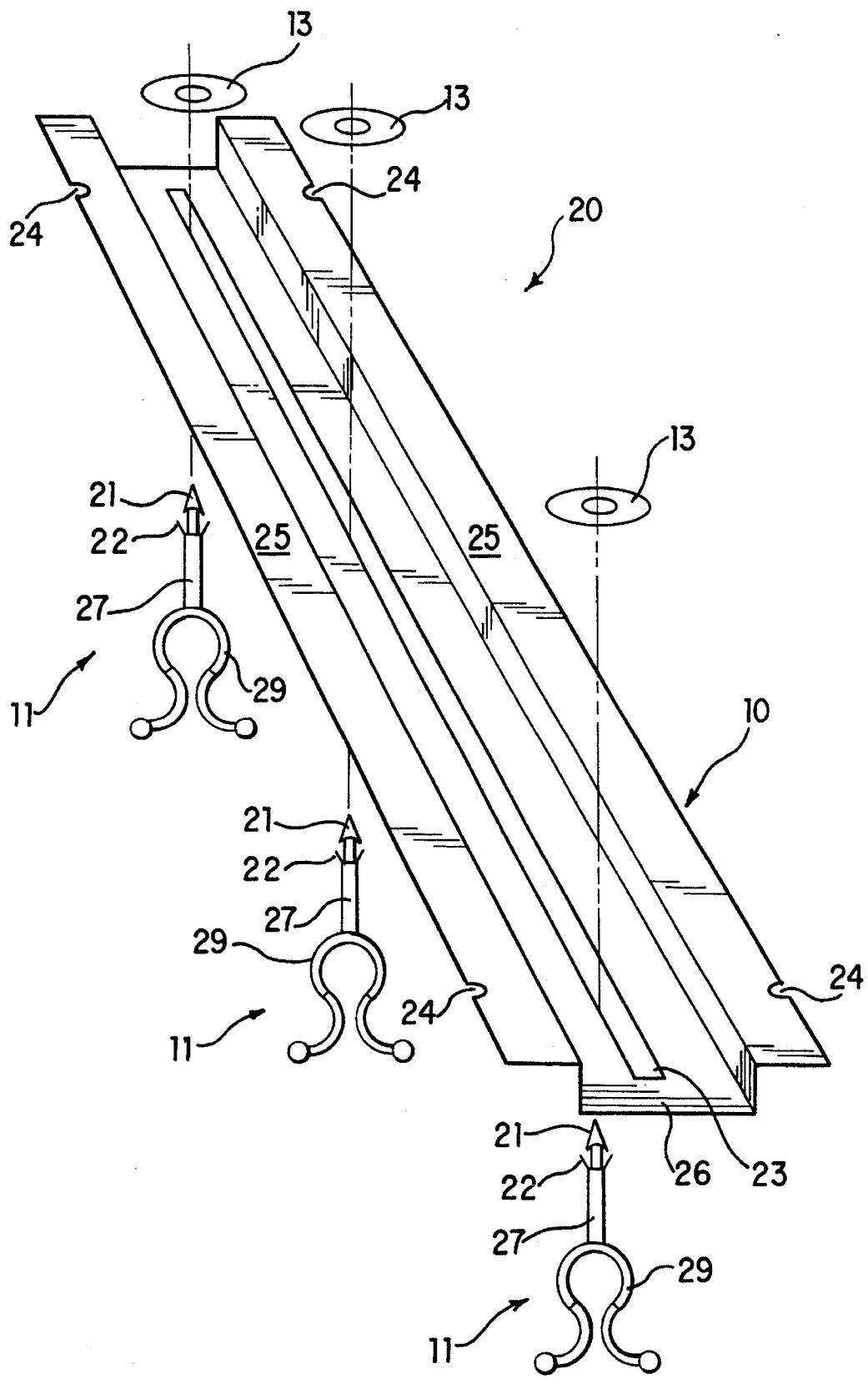
FIG. 3 shows an exploded view of the cable management system of FIG. 2 that is constructed in accordance to the illustrated preferred embodiment of the present invention.

FIG. 3 shows an exploded view of the cable management system 20 that is constructed in accordance to the illustrated preferred embodiment of the present invention. A slot assembly 10 is formed of metal, plastic or other material. The slot assembly 10 is attached to a surface of the ultrasound imaging system with screws or other fasteners (not shown) positioned in cut-outs 24 formed in side flanges 25 of the slot assembly 10. Alternatively, the slot assembly 10 is integrated into a part of the ultrasound imaging system, such as a service tray 14.

The slot assembly 10 accommodates multiple retaining clips 11 within a slotted aperture 23 cut in a trough 26. The retaining clips 11 such as those available from ITW Corporation, part number 232-120207-20 are held in place by retaining rings 13. A barb 21 terminates a shaft 27 attached to a clasp 29 of each retaining clip 11. The barb 21 penetrates the annular shaped retaining ring 13 and is captively held within the retaining ring 13 by the barb 21 and a flange 22 located along the shaft 27. The shape of the retaining ring 13 allows pivotal rotation of the retaining clip 11. The clasp 29 and the fastener, which includes the retaining ring 13, barb 21, shaft 27 and flange 22, are slidably held within the slotted aperture 23 of the slot assembly 10.

Other fasteners for slidably holding the retaining clips 11 in the slotted aperture 23 are also feasible. For example, the retaining clip 11 may not have the barb 21 and the flange 22. A screw threaded into the shaft 27 and a washer positioned below the slotted aperture 23 in place of the flange 22, would also hold the retaining clip 11 in a slidably mounted fashion within the slotted aperture 23. The screw would replace the function of the barb 21 and retaining ring 13, while the washer would replace the function of the flange 22.

Other embodiments of the invention will be apparent to the skilled in the art from a consideration of this specification or practice of the invention disclosed herein. It is intended that the specification and examples be considered as exemplary only, with the true scope and spirit of the invention being indicated by the following claims.

I claim:

1. A mobile ultrasound imaging system for obtaining ultrasound images of a patient's body, comprising:

multiple transducer probes, each of the multiple transducer probes for ultrasonically interrogating the patient's body:

a cable array, each cable of the cable array connecting to a corresponding transducer probe at a first end and connecting to the mobile ultrasound imaging system at a second end;

a display for generating an ultrasound image based on the ultrasonic interrogation;

a cable management system, slidably securing each cable of the cable array to the mobile ultrasound imaging system;

a slot assembly having a slotted aperture, attached to the mobile ultrasound imaging system;

multiple clasps, each clasp removably attached to a corresponding cable of the cable array; and multiple fasteners for slidably retaining the clasps within the slotted aperture.

2. The mobile ultrasound imaging system of claim 1 wherein the cable management system further comprises at least one mounting rod protruding from the mobile ultrasound imaging system for mechanically supporting cables within the cable array.

3. A mobile ultrasound imaging system for obtaining ultrasound images of a patient's body, comprising:

multiple transducer probes, each of the multiple transducer probes for ultrasonically interrogating the patient's body;

a cable array, each cable of the cable array connecting to a corresponding transducer probe at a first end and connecting to the mobile ultrasound imaging system at a second end;

a display for generating an ultrasound image based on the ultrasonic interrogation;

a cable management system, slidably securing each cable of the cable array to the mobile ultrasound imaging system;

a tray having a top surface and a bottom surface, the tray attached to the mobile ultrasound imaging system and protruding from the mobile ultrasound imaging system;

a slot assembly having a slotted aperture, attached to the bottom surface of the tray;

multiple clasps, each clasp removably attached to a corresponding cable of the cable array; and multiple fasteners for slidably retaining the clasps within the slotted aperture.

4. The mobile ultrasound imaging system of claim 3 further comprising a mounting hook attached to the bottom surface of the tray for mechanically supporting cables within the cable array.

5. A cable array for connecting multiple transducer probes to an ultrasound imaging system, comprising:

multiple transducer cables, each of the multiple transducer cables corresponding to one of the multiple transducer probes;

a slot assembly having a slotted aperture, attached to the ultrasound imaging system;

multiple clasps, operative to removably attach to the transducer cables; and multiple fasteners for slidably retaining the clasps within the slotted aperture.

6. The cable array of claim 5 wherein each of the multiple fasteners further comprises:

a shaft attached at a first end to each of the clasps;

a barb incorporated into a second end of the shaft;

a flange positioned between the first and the second ends; and an annular retaining ring on an inner side of the slotted aperture, penetrated by the barb from an outer side of the slotted aperture, captively engaged between the barb and flange.

7. A cable management system for collating multiple cables connecting to a mobile ultrasound imaging system, comprising:

a slide assembly having a slotted aperture, attached to the ultrasound imaging system;

multiple clasps, adapted for removably attaching to the multiple cables; and multiple fasteners for slidably retaining the clasps within the slotted aperture.

8. The cable management system of claim 7 wherein each of the multiple fasteners comprises:

a shaft attached at a first end to each of the clasps;

a barb incorporated into a second end of the shaft;

a flange positioned between the first and second ends; and an annular retaining ring on an inner side of the slotted aperture, penetrated by the barb from an outer side of the slotted aperture, captively engaged between the barb and flange.

9. The cable management system of claim 7 further comprising a mounting rod protruding from the ultrasound imaging system for mechanically supporting at least one of the multiple cables.

* * * * *